(12) United States Patent
Demas et al.

(10) Patent No.: US 8,614,575 B2
(45) Date of Patent: Dec. 24, 2013

(54) NMR, MRI, AND SPECTROSCOPIC MRI IN INHOMOGENEOUS FIELDS

(75) Inventors: Vasiliki Demas, Oakland, CA (US);
Alexander Pines, Berkeley, CA (US);
Rachel W. Martin, Irvine, CA (US);
John Franck, Berkeley, CA (US);
Jeffrey A. Reimer, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 1103 days.

(21) Appl. No.: 11/917,639

(22) PCT Filed: Jun. 16, 2006

(86) PCT No.: PCT/US2006/023787
§ 371 (c)(1),
(2), (4) Date: Jan. 12, 2010

(87) PCT Pub. No.: WO2008/024092
PCT Pub. Date: Feb. 28, 2008

(65) Prior Publication Data
US 2010/0102811 A1 Apr. 29, 2010

Related U.S. Application Data

(60) Provisional application No. 60/691,733, filed on Jun. 17, 2005, provisional application No. 60/709,249, filed on Aug. 16, 2005.

(51) Int. Cl.
*G01V 3/00* (2006.01)
(52) U.S. Cl.
USPC .......................................... 324/309; 324/307
(58) Field of Classification Search
USPC .................... 324/300–322; 600/407–445
See application file for complete search history.

(56) References Cited

U.S. PATENT DOCUMENTS

| 4,968,939 A | 11/1990 | Pines et al. |
| 6,159,444 A * | 12/2000 | Schlenga et al. ............... 424/9.3 |
| 6,426,058 B1 | 7/2002 | Pines et al. |

(Continued)

OTHER PUBLICATIONS

Demas et al., "Three-Dimensional Phase-Encoded Chemical Shift MRI in the Presence of Inhomogeneous Fields", Proceedings of the National Academy of Sciences, vol. 101, No. 24, pp. 8845-8847, (Jun. 15, 2004).

(Continued)

*Primary Examiner* — Brij Shrivastav
(74) *Attorney, Agent, or Firm* — Lawrence Berkeley National Laboratory

(57) ABSTRACT

A method for locally creating effectively homogeneous or "clean" magnetic field gradients (of high uniformity) for imaging (with NMR, MRI, or spectroscopic MRI) both in in-situ and ex-situ systems with high degrees of inhomogeneous field strength. The method of imaging comprises: a) providing a functional approximation of an inhomogeneous static magnetic field strength $B_0(\vec{r})$ at a spatial position $\vec{r}$; b) providing a temporal functional approximation of $\vec{G}_{shim}(t)$ with i basis functions and j variables for each basis function, resulting in $v_{ij}$ variables; c) providing a measured value $\Omega$, which is an temporally accumulated dephasing due to the inhomogeneities of $B_0(\vec{r})$; and d) minimizing a difference in the local dephasing angle $\phi(\vec{r},t)=\gamma \int_0^t \sqrt{|\vec{B}_1(\vec{r},t')|^2+(\vec{r}\cdot\vec{G}_{shim}G_{shim}(t')+\|\vec{B}_0(\vec{r})\|\Delta\omega(\vec{r},t')/\gamma)^2}dt'-\Omega$ by varying the $v_{ij}$ variables to form a set of minimized $v_{ij}$ variables. The method requires calibration of the static fields prior to minimization, but may thereafter be implemented without such calibration, may be used in open or closed systems, and potentially portable systems.

13 Claims, 11 Drawing Sheets

(56) References Cited

U.S. PATENT DOCUMENTS

| | | |
|---|---|---|
| 6,652,833 B2 | 11/2003 | Pines et al. |
| 6,674,282 B2 | 1/2004 | Pines et al. |
| 6,818,202 B2 | 11/2004 | Pines et al. |
| 6,885,192 B2 | 4/2005 | Clarke et al. |
| 6,965,232 B2 * | 11/2005 | Sodickson .................... 324/307 |
| 7,586,306 B2 * | 9/2009 | Szyperski et al. ............ 324/309 |
| 2012/0265050 A1 * | 10/2012 | Wang ............................ 600/411 |

OTHER PUBLICATIONS

Weitekamp et al., "High-Resolution NMR Spectra in Inhomogeneous Magnetic Fields: Applications of Total Spin Coherence Transfer Echoes", Journal of the American Chemical Society, vol. 103, pp. 3578-3579, (1981).

Demco et al., "NMR Imaging of Materials", Current Opinion in Solid State and Materials Science, vol. 5, pp. 195-202, (2001).

Balbach, et al., "High-Resolution NMR in Inhomogeneous Fields", Chemical Physics Letters, vol. 277, pp. 367-374, (1997).

Meriles, et al., "Approach to High-Resolution ex Situ NMR Spectroscopy", Science, vol. 293, pp. 82-85, (Jul. 6, 2001).

Heise, et al., "Two-Dimensional High-Resolution NMR Spectra in Matched Bo and B1 Field Gradients", Journal of Magnetic Resonance, vol. 156, pp. 146-151, (2002).

Meriles, et al., "Broadband Phase Modulation by Adiabatic Pulses", Journal of Magnetic Resonance, vol. 164, pp. 177-181, (2003).

Sakellariou, et al., "Advances in Ex-Situ Nuclear Magnetic Resonance", Comptes Rendus Academie des Sciences Physique, vol. 5, pp. 337-347, (2004).

Topgaard, et al., "'Shim Pulses' for NMR Spectroscopy and Imaging", Proceedings of the National Academy of Sciences, vol. 101, No. 51, pp. 17576-17581, (Dec. 21, 2004).

Perlo, et al., "High-Resolution NMR Spectroscopy with a Portable Single-Sided Sensor", Science, vol. 308, pp. 1279. (May 27, 2005).

Norris, "Adiabatic Radiofrequency Pulse Forms in Biomedical Nuclear Magnetic Resonance", Max-Planck-Institute of Cognitive Neuroscience, vol. 14, No. 2, pp. 89-101, (2002).

International Search Report and Written Opinion for International Application No. PCT/US2006/023787 mailed Mar. 28, 2008.

* cited by examiner

500

NMR, MRI, AND SPECTROSCOPIC MRI IN INHOMOGENEOUS FIELDS

CROSS REFERENCE TO RELATED APPLICATIONS

This patent application claims benefit of priority to U.S. provisional patent application 60/691,733 filed Jun. 17, 2005, U.S. provisional patent application 60/709,249 filed Aug. 16, 2005, and PCT patent application PCT/US2006/023787, filed Jun. 16, 2006, all of which are hereby incorporated by reference in their entireties.

STATEMENT REGARDING FEDERAL FUNDING

This invention was made with U.S. Government support under Contract Number DE-AC02-05CH11231 between the U.S. Department of Energy and The Regents of the University of California for the management and operation of the Lawrence Berkeley National Laboratory. The U.S. Government has certain rights in this invention.

BACKGROUND OF THE INVENTION

1. Field of the Invention

The present invention pertains generally to methods used in nuclear magnetic resonance imaging (MRI) and nuclear magnetic resonance (NMR), and more specifically to NMR, MRI, or spectroscopic MRI in inhomogeneous magnetic fields.

2. Description of the Relevant Art

What follows is a brief introduction to some NMR basics, with the intention of describing some of the terminology used in this disclosure.

Magnetic resonance spectroscopy and imaging require that a sample be subjected to a static magnetic field $\vec{B}_0$. Units of field strength are in Tesla (T), where 1T is $10^4$ Gauss. Typically the static field is produced by a superconducting magnet, or, as in the case of portable systems, by permanent magnets or electromagnets. Nuclei that possess spin (this is an intrinsic property like charge and mass, and one can think of it as an intrinsic angular momentum) can be studied with NMR (e.g. $^1H$, $^{13}C$, $^{19}F$), though most people are familiar with (hydrogen nucleus $^1H$) proton MR. In the absence of a field, nuclear magnetic moments (nuclear magnetic moment is associated with spin) are random because all allowed orientations have the same energy. When the sample is placed in the strong magnetic field, a macroscopic magnetization parallel to the field appears.

The second requirement for MR experiments is to excite the sample. This is done by a second field, $\vec{B}_1$ perpendicular to the static field $\vec{B}_0$. This $\vec{B}_1$ field is generally produced by sending radio frequency (or RF) current through a coil, most typically a solenoid or a saddle coil and producing a magnetic field $\vec{B}_1$, which oscillates at the Larmor frequency ($\omega_0 = \gamma B_0$), where gamma is the gyromagnetic ratio which is characteristic of the nucleus and has units of Frequency/field strength). For this reason in NMR, people prefer using frequency units when referring to field strength magnitude. For example, a 2.3 T magnet would be referred to as a 100 MHz magnet, because 100 MHz is the resonance frequency of the $^1H$ hydrogen nucleus in the reference compound (TMS) in that field.

One needs to have a homogeneous static magnetic field over the sample, so that it is easy to determine the microenvironment. If the field is inhomogeneous (i.e. $\vec{B}_0(\vec{x})$ depends on position in space), local environment effects are negligible relative to $\vec{B}_0(\vec{x})$ variations.

The local environment depends on the electronic cloud surrounding the nucleus, and the effect is called shielding, s (imagine that the electrons "protect" the nucleus from the static field). Chemical shift is the NMR chemical signature of a substance, which is the variation of the resonance frequency because of shielding $\Omega_0 = \gamma B_0(1-\sigma)$. NMR spectroscopists like to measure chemical shifts, as the difference from a standard, $\Delta\omega = \gamma B_0 \Delta\sigma = \gamma B_0(\sigma_{ref} - \sigma)$ in units of parts per million (ppm). Sometimes inhomogeneities or gradients (variations of field for variations of space) in a magnet are measured in ppms, since this is the scale of most importance for NMR measurements.

Traditional measurements of samples using the physical process of magnetic resonance, both nuclear magnetic resonance (NMR) and magnetic resonance imaging (MRI) utilize static magnetic $\vec{B}_0$ fields of high uniformity, typically maintaining homogeneity of 10-100 parts per billion (ppb) within a sampling volume intended to be tested.

U.S. Pat. No. 6,674,282 describes a method and apparatus for ex-situ nuclear magnetic resonance spectroscopy for use on samples outside the physical limits of the magnets in inhomogeneous static and radio-frequency fields, which is hereby incorporated by reference in its entirety. Chemical shift spectra can be resolved with the method using sequences of correlated, composite z-rotation pulses in the presence of spatially matched static and radio frequency field gradients producing nutation echoes. The amplitude of the echoes is modulated by the chemical shift interaction and an inhomogeneity free FID (free induction decay) may be recovered by stroboscopically sampling the maxima of the echoes. In an alternative embodiment, full-passage adiabatic pulses are consecutively applied. One embodiment of the apparatus generates a static magnetic field that has a variable saddle point.

Additionally, and by way of background, U.S. Pat. Nos. 4,968,939, 6,426,058, 6,818,202, 6,159,444, 6,652,833, and 6,885,192 are also incorporated by reference in their entireties.

BRIEF SUMMARY OF THE INVENTION

In one embodiment, a method of imaging, comprising: a) establishing a $\vec{B}_0$ field of known strength; b) modulating a $\vec{B}_1$ field of known strength produced by an radio frequency (RF) signal; c) modulating a $\vec{G}_{shim}(\vec{r},t)$ field; where $\vec{G}_{shim}(\vec{r},t)$ is a gradient field that is a function of: (1) a position vector $\vec{r}$, and (2) a time t; d) forming an effective field $\vec{B}_{EFF}(\vec{r},t)$ from a superposition of effects from the $\vec{B}_0$, $\vec{B}_1$, and $\vec{G}_{shim}(\vec{r},t)$ fields; and e) minimizing a dephasing of a sample volume acted upon by $\vec{B}_{EFF}(\vec{r},t)$ by modulating the $\vec{B}_1$, and $\vec{G}_{shim}(\vec{r},t)$ fields, the modulating subject to at least one constraint.

In alternate embodiments, $\vec{r}$ is a one, two, or three dimensional position vector. Commensurately, the term "volume" is respectively a line, area, and traditional three-dimensional volume.

$\vec{B}_0$ is typically produced by a magnet, which may be a permanent magnet, traditional room-temperature electromagnet, or superconductive electromagnet.

The RF signal producing $\vec{B}_1$ is typically produced by an RF signal either capacitively or inductively coupling through an antenna.

$\vec{G}_{shim}(\vec{r},t)$ is a gradient field. The gradient field is a function of its spatial (in the one-, two-, and three-dimensional sense) location, and time. The gradient field is typically produced by an electromagnetic coil. Such electromagnetic coils may be referred to as "imaging coils". In one embodiment here, the specific coil is a "ladder" coil that exhibits increasing field strength as more coils are added to a region. The "ladder" coil, as further described below, is in description rectangular in nature, however may alternatively be made in other geometries so as to generate desired known gradient field strengths. The gradient thus resulting from a ladder coil is typically linearly varying over a spatial direction independent of other fields.

One of the most efficient ways to perform NMR and MRI is to always use orthogonal linearly varying fields, but non-orthogonal fields may also be used with appropriate adjustments. In one embodiment described below, the gradient field is a simple coil, producing a magnetic field that falls off in a known non-linear fashion the further from the coil. By placement of one such coil and two perpendicular ladder coils, one is able to produce arbitrary gradients in separate $\vec{x}$, $\vec{y}$ and $\vec{z}$ directions in three-dimensional space. The gradient fields may be made to be spatially varying in a linear, non-linear, or constant fashion. By altering or modifying a current fed to each of these coils, the field produced by the coils may be made a function of time t. Gradient fields are widely used in NMR and MRI in medical applications for the imaging of human and animal anatomy.

The "known strength" referred to herein means that the field strength has been calibrated, either by direct MRI resonance mapping of a suitable spin sample, such as a proton (in $H_2O$ typically), or by a combination of measurement and modeling. Typically, actual resonance mapping is found to be most accurate. In alternate embodiments, field strength may be calibrated by interspersing a conical coil of known configuration to generate a known gradient.

Portable NMR sensors could be inexpensive and robust, potentially making them easy to use in the field to scan suspicious objects, and thereby non-destructively identifying the composition of the objects. A portable NMR, MRI, or spectroscopic MRI sensor could become standard equipment in clinics and ambulances, thus expediting patient diagnosis, especially where such quick diagnosis is critical, such as in spinal/neck injuries and strokes/brain traumas. Portable NMR, MRI, or spectroscopic MRI devices could be placed a vehicle for operation in the field, factories, museums, monuments, etc. If the sample cannot be moved to the magnet, then the magnet could be transported to the sample.

In the particular instance of head trauma and stroke detection, it may be desirable to construct ex-situ magnets that partially wrap around the space where a head would be placed for imaging. Such a magnet may in fact form somewhat of a "U shape" around the head, with the head inserted on some cushioning material. In this sense, this type of magnet may be referred to as a "pillow magnet". These pillow magnets may be configured as portions of cylindrical walls, biconvex, planar, spherical, or other aspheric geometries. Such pillow magnets may most advantageously be configured in a Halbach configuration to minimize extraneous external fields and maximize test region fields.

The methods taught here increases the useful sample volume of a homogeneous field or the field of linear gradient, while resulting in hardware that can be less expensive and easier to construct than traditional devices. These methods could be used to improve the possible applications of NMR/MRI with setups employing permanent magnets (either single sided, or closed geometries such as Halbach magnets), electromagnets, or superconducting magnets (inside a bore or in a stray field, single sided design).

A one-sided sensor offers open access to samples of arbitrary size, empowering NMR to be used for application such as the chemical identification of concealed explosives, energetic materials, and biohazards in various setups. Portable NMR sensors may be made inexpensive and robust, making it easy for them to be used in the field to scan suspicious objects, after a first screening, and then non-destructively identify the composition of the object.

BRIEF DESCRIPTION OF THE SEVERAL VIEWS OF THE DRAWINGS

The invention will be more fully understood by reference to the following drawings, which are for illustrative purposes only.

DETAILED DESCRIPTION

Defined Terms

Figure 1A:
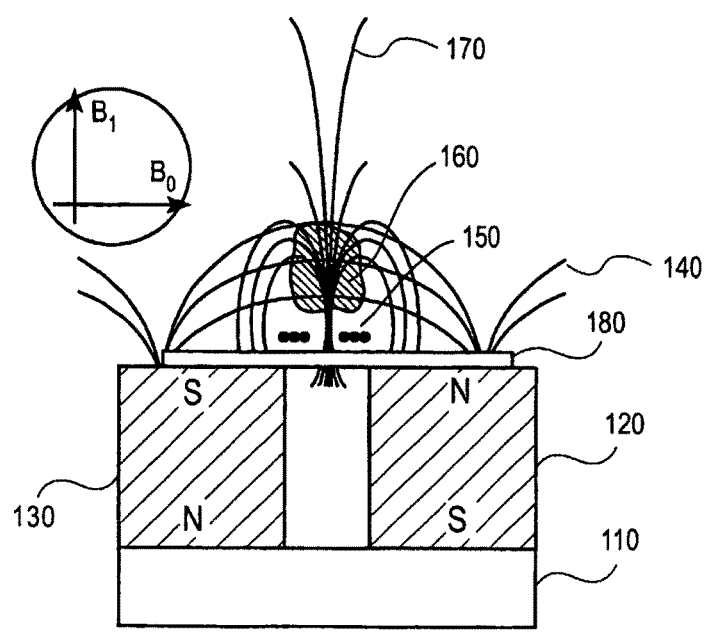
FIG. 1A is a U-shaped type magnet system for one-sided NMR, MRI, or spectroscopic MRI.

Computer means any device capable of performing the steps developed in this invention, including but not limited to: a microprocessor, a digital state machine, a field programmable gate array (FGPA), a digital signal processor, a collocated integrated memory system with microprocessor and analog or digital output device, a distributed memory system with microprocessor and analog or digital output device connected with digital or analog signal protocols.

Computer readable media means any source of organized information that may be processed by a computer to perform the steps developed in this invention, but not limited to: a magnetically readable storage system; optically readable storage media such as punch cards or printed matter readable by direct methods or methods of optical character recognition; other optical storage media such as a compact disc (CD), a digital versatile disc (DVD), a rewritable CD and/or DVD; electrically readable media such as programmable read only memories (PROMs), electrically erasable programmable read only memories (EEPROMs), field programmable gate arrays (FGPAs), flash random access memory (flash RAM); and remotely transmitted information by electromagnetic or optical methods.

Inhomogeneous means nonuniform, or an otherwise non-constant value. In the context here, it means a magnetic field, which over a sample region, has a nonuniform magnitude of vector components as spatial locations are varied.

Introduction

This application describes methodologies and apparatus to improve NMR, MRI, or spectroscopic MRI resolution in the presence of static field inhomogeneities, either inside the bore of a poorly shimmed magnet, or in a one-sided system where the geometry of the magnet naturally creates a field distribution. In conventional NMR a great deal of time, effort, and cost is spent on building extremely homogeneous magnets (shim coils are employed to improve further the homogeneity) and gradient coils for imaging that have a very well defined spatial dependence (for example a gradient along $\vec{x}$ that has a linear dependence in the x direction, but is the same for different $\vec{y}$ or $\vec{z}$ positions over the sample). The reason for these stringent requirements is that the nuclear magnetic resonance signal depends on the value of the field and that the gradients are used to encode spatial information, so there has to be a "clean" frequency- and thus magnetic field-space correlation. Field inhomogeneities lead to line broadening and loss of spectral information, while imperfect imaging gradients have, in the past caused imaging artifacts.

Methods are proposed here that may be used to recover spectral information lost due to field imperfections in either ex-situ (outside of the magnet) or in-situ (inside an inhomogeneous magnet) configurations. In the first case, which is named "ex-situ", matching exploits a radio frequency field inhomogeneity that is designed to reproduce the static field variations and subsequently induce nutation echoes whose phase is only sensitive to chemical shift differences. Sampling of the echo maxima leads to high-resolution NMR spectra. The second method, which is named "shim pulses", uses a combination of specially crafted RF pulses and time modulated gradient pulses to obtain refocusing of static field inhomogeneities left after shimming. In one embodiment, ex-situ matching and shim pulses for both ex-situ and in-situ environments are combined, to allow the capture of both NMR spectroscopic and imaging information. This techniques yields resultant effective fields that are either homogeneous, or have a linear dependence in one or more spatial dimensions, alleviating the need to make perfect one sided gradients, or perfect RF matching coils. An example of single sided imaging gradient coils that produce "clean" transverse field gradients is presented. Such gradients can be used both for in-situ and ex-situ magnet configurations Method 1: Hardware Correction for Single-Sided Imaging Gradients for Ex-Situ Imaging FIGS. 1A-D depict various magnetic structures usable for ex-situ and in-situ NMR, MRI, and spectroscopic MRI. These designs are only a small summary of those usable with the techniques disclosed herein, but there are several other possibilities.

Figure 1B:
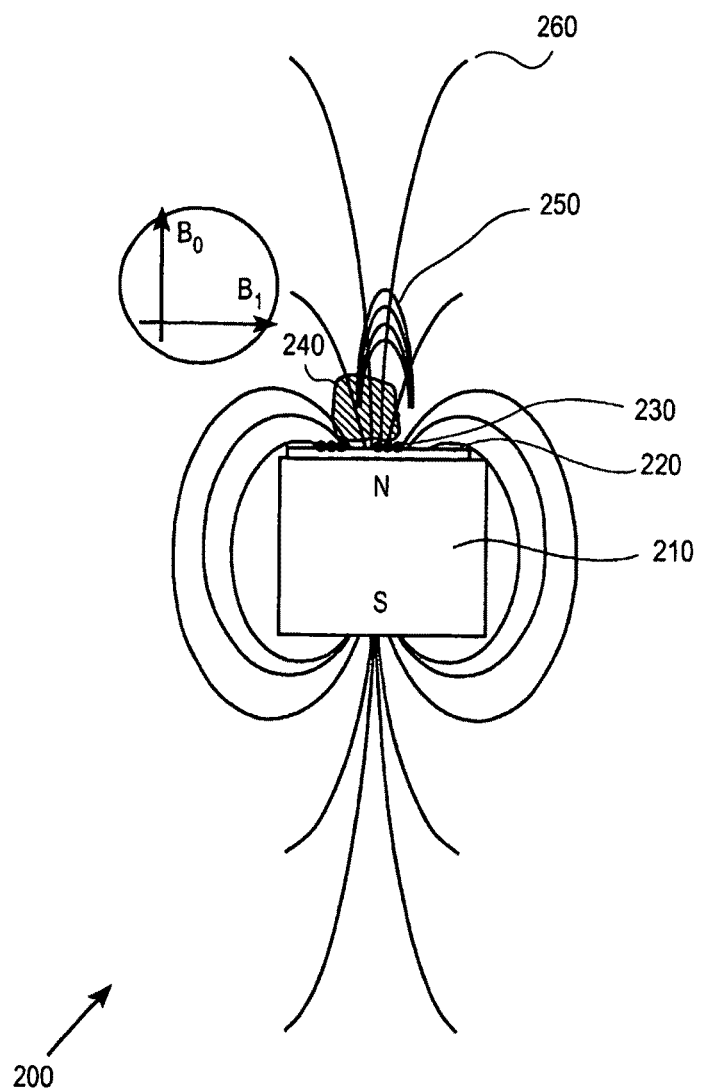
FIG. 1B is one example of the generalized Halbach magnet family whereby static fields are produced by arrangement of polarized arrays. In this case a dipolar array with internal flux is shown.

Field corrections may be necessary in single sided systems, such as those shown in FIG. 1A and FIG. 1B. These are the two most simple permanent magnet configurations of a U-shaped system and a dipole respectively. While the sample and RF electronics are shown to be in the one side of the magnet, this is not necessary. Depending on the polarity of the two poles shown in FIG. 1A, the "sweet spot" of the field may be in the center of the magnet and therefore the sample may be placed within the two poles. Other single-sided units can be used, with multiple elements either arranged in a Halbach sheet or in other ways to give a desired magnetic field profile that can be further improved with this technique.

In particular, FIG. 1A shows an NRM/MRI system 100 comprising two magnets 120, 130 coupled by a yoke material 110 so as to form a magnetic circuit with field lines 140 leaving the structure. A coil 180 supplies a gradient, and an RF coil set 150 provides fields 170 that pass through a sample 160.

FIG. 1B shows just a single simple magnet system 200 that comprises a one-sided magnet 210 that produces external field lines 250 that pass through a sample 240. Similarly to FIG. 1A, there is a coil 220 that provides a gradient, and an RF coil 230, both coils providing fields that pass through the sample 240.

Figure 1C:
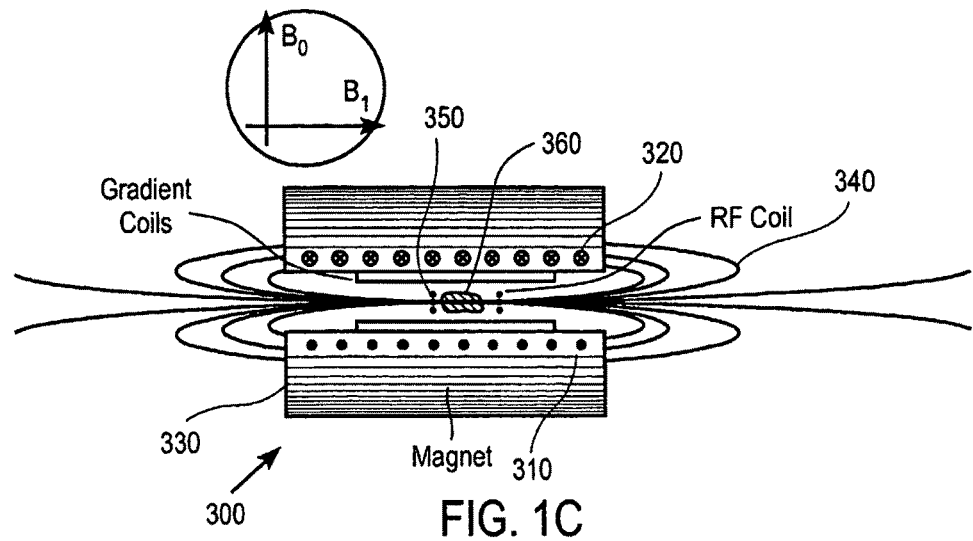
FIG. 1C is another general single-sided magnet.

FIG. 1C shows a cylindrical superconducting magnet system 300, where the field initially is relatively homogeneous. However NMR/MRI may be further improved by minimizing dephasing error due to the inhomogeneities. Additionally, an electromagnet, or a permanent magnet cylinder, or other closed configurations may be used. Here, superconducting magnet 310 is providing a field that comes up 310 and goes back down 320 through magnet body 330, producing magnetic fields 340. A sample 360 is shown in the bore of the magnet 330, which is excited by RF coil 350 and gradient coils 380. The sample and RF electronics are shown to be internal, but the technique and experiments can be performed in the stay field of the magnet.

Figure 1D:
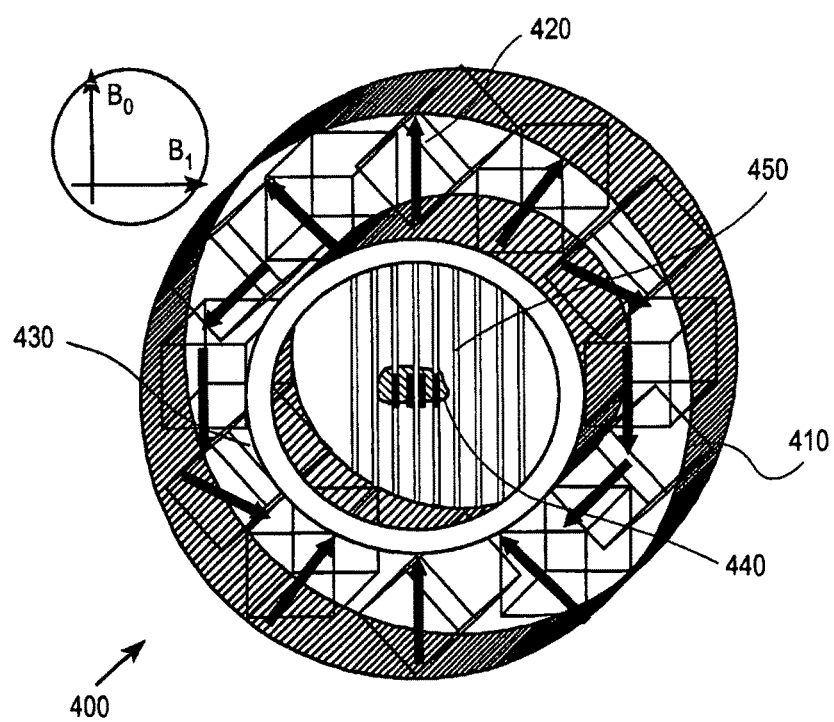
FIG. 1D shows the inside of a standard superconducting magnet, with imperfect gradient coils and/or imperfect shimming.

FIG. 1D shows a permanent magnet array system 400 in a Halbach configuration, resulting in the characteristic Halbach internal dipolar flux. Here the overall Halbach magnet 410 is comprised of many individual magnets in varying orientation 420. A gradient coil 430 is interior to the Halbach array, where RF probe coil 450 surrounds a sample 440. The sample and RF coils are shown inside the magnet. The technique can be used for other array configurations, producing a static field inside the arrangement (e.g. quadrupolar flux arrays).

Figure 2A:
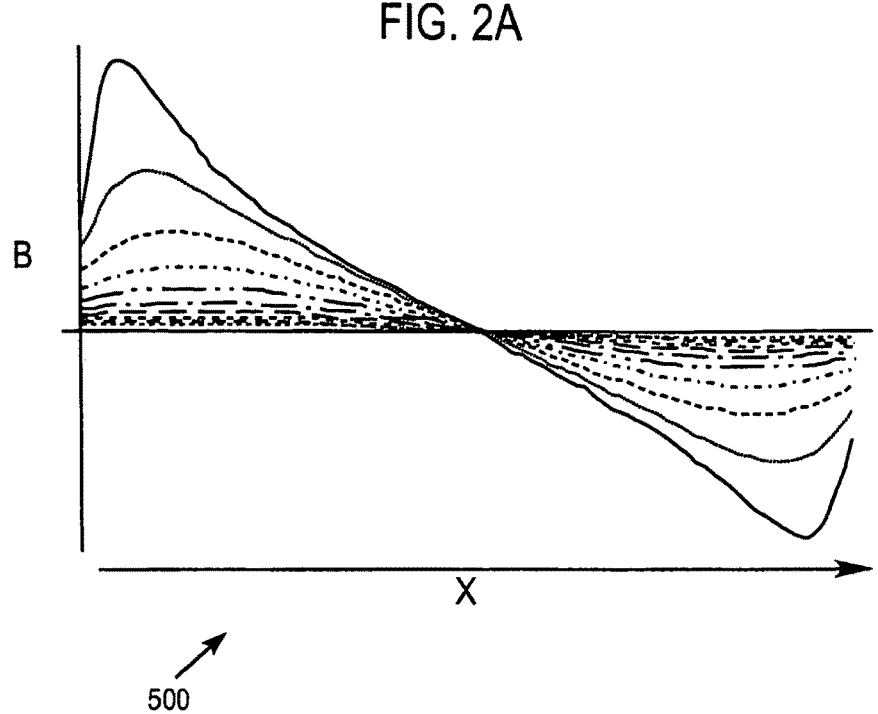
FIG. 2A shows the field strength calculated from a single one-sided gradient coil arrangement example (double ladder). [The field produced is linear over a region, as desired for MRI. However, there is an additional decay of the field as one moves away from the coils. By placing a rotated second identical coil with opposed current, the z dependence is largely eliminated.]
Figure 2B:
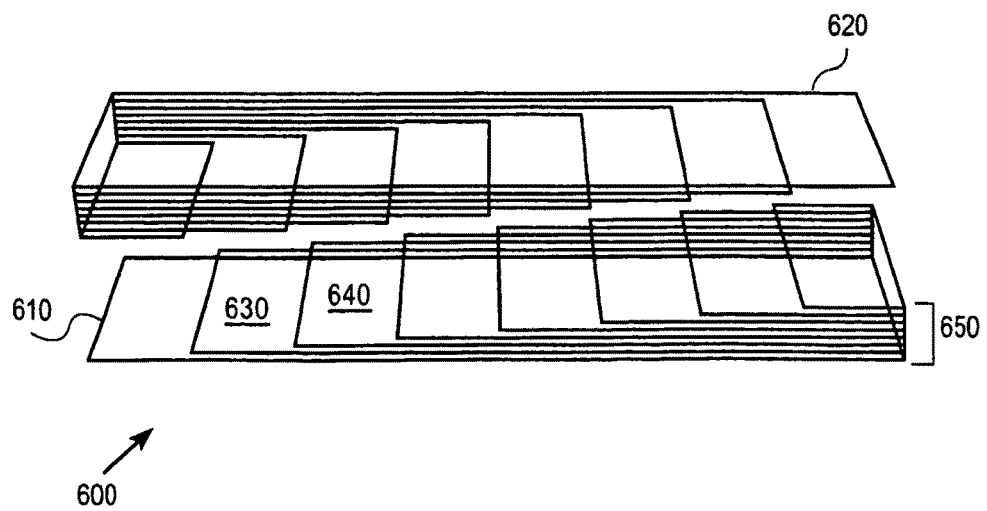
FIG. 2B is a diagram of the coil-winding pattern for the ladder coil previously used for calculation in FIG. 2A.

FIG. 2A shows the combination of field strengths that are achieved by a multiplicity of individual loop coils shown in FIG. 2B. One strategy for ex-situ matching and shimming involves designs of single sided gradient coils. One example of gradient coils that can be used to image a transverse plane (a plane perpendicular to the main field) are double ladder coils (as shown in FIG. 2B) positioned under the sample and below the radio frequency coil. The RF ladder of FIG. 2B, 600, is comprised of a first loop 610 added to a second loop 620, and a third loop 630, ultimately stacking into a group of loops 650 on one side of the array. Similarly, initial bottom loop 610 is duplicated above at 620, to begin the formation of a mirrored and rotated loop above. The net result of the fields generated by this geometry results in the Fields plots shown in FIG. 2A. These imaging coils produce substantially linear gradients along their length, with their field passing through zero at the center of the coils. However, inherently these gradients have a coupling with the direction perpendicular to the coil (z), due to their one-sided conformation. If a second set of identical gradients at a vertical distance δz from the first set of coils with current flowing in opposite direction is used, one can correct for the unwanted z-gradient coupled with the transverse gradient.

Figure 2C:
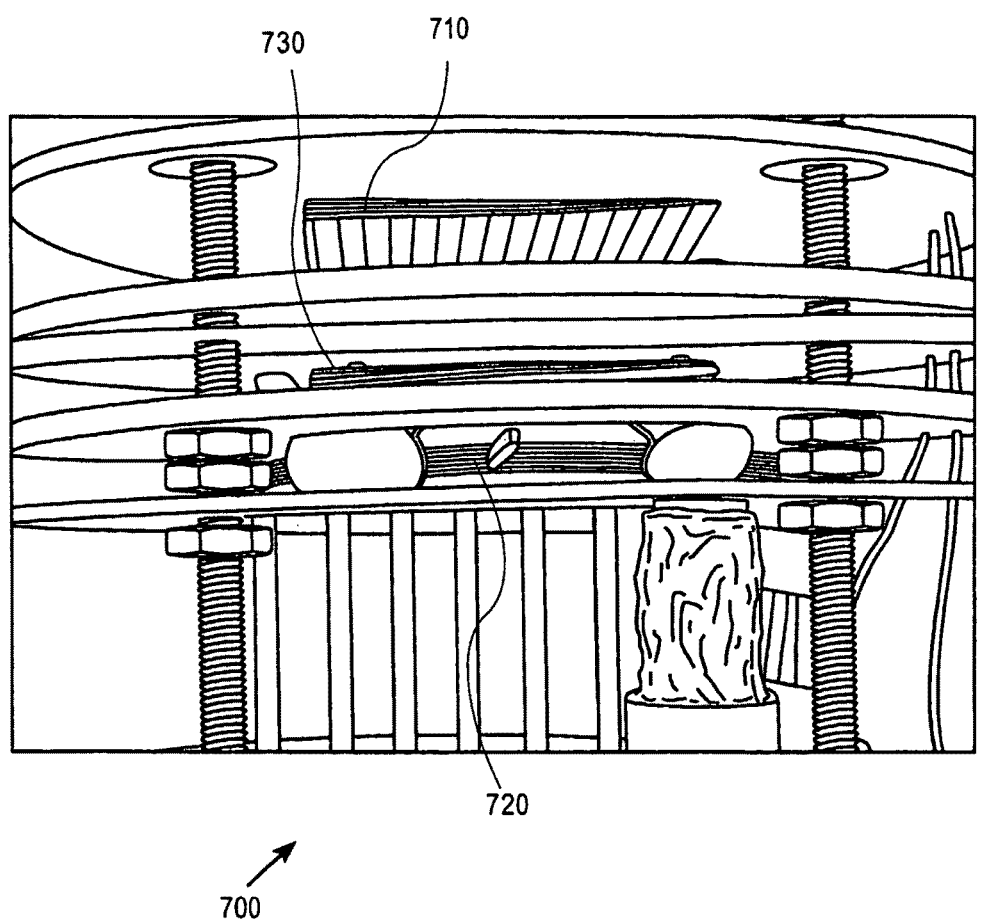
FIG. 2C is an illustration of one embodiment of a ladder coil previously illustrated in FIG. 2B. It is readily apparent that the structure of the coil is very similar to the coil diagram in FIG. 2B.

FIG. 2C is a sketch of one implementation 700 of a pair of imaging single sided gradient coils, based on the design of FIG. 2B. The design in used here is a combination of two straight forward ladder coils that can be used to ensure that the gradient field is zero at the center of the sample and is symmetric along the length of the gradient. The spacing of the steps may be altered in a non-linear fashion to improve the profile. Here RF coil 720 is placed in close proximity to an upper 710 and lower 730 ladder coil.

Figure 3A:
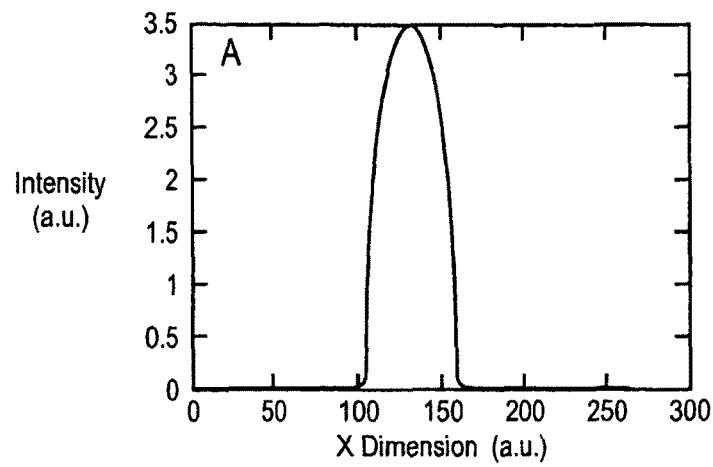
FIG. 3A shows the results of density matrix calculations of a one-dimensional imaging experiment in the case where a standard gradient is present (the gradient depends on one coordinate). Here, a standard model of a one-dimensional sphere is used. It is assumed that a "perfect" linear gradient is used.
Figure 3B:
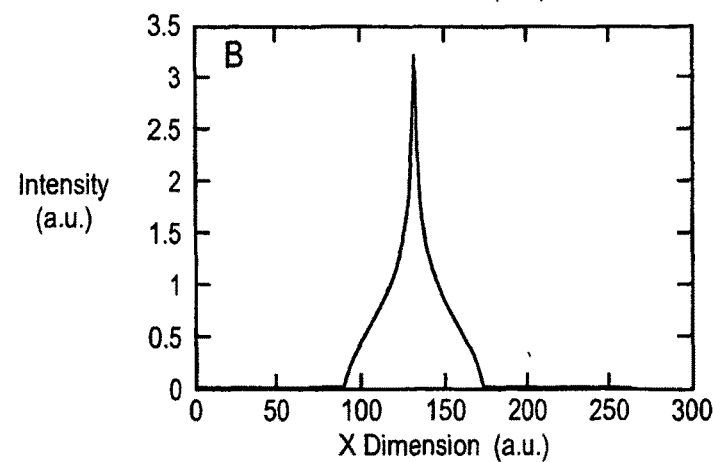
FIG. 3B shows the results of density matrix calculations of the one-dimensional imaging experiment for the sphere model of FIG. 3A where the gradient has a dependence on more than one coordinate, as would be the case for single-sided gradient.
Figure 3C:
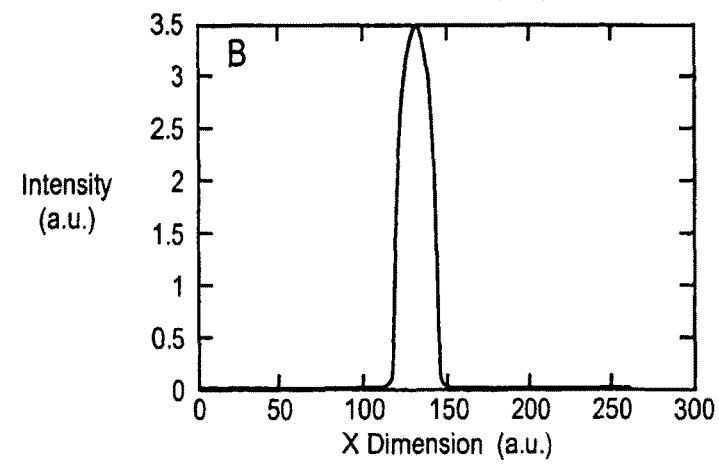
FIG. 3C shows the corrected image results of a density matrix calculation of a one-dimensional imaging experiment imaged by "double" single-gradients, i.e. two identical sets of coils whose combined field is a pure one-dimensional gradient. One can extrapolate this technique to other single sided gradient coils. The same effect can also be generated by a single set of gradient coils by applying a second dc pulse, with inverted direction and scaled current amplitude.

FIGS. 3A-C show a model response from a standard 1D image of a spherical object when a constant gradient is applied. This is as expected from the principles described in MR textbooks. FIG. 3B shows how the 1D image of the same sample looks when the gradient is as described in FIG. 2A, where there is an x gradient (the imaged dimension), but the strength of the gradient also depends on the distance from the coil (z direction). The image is obviously distorted. FIG. 3C shows the recovered image, which can be used by adding a second, identical pair of coils at a finite distance from the one described in FIG. 3B, or in the case of any other single sided gradient coils. The correction can also be achieved via use of the technique described in the main body of the text.

Figure 3D:
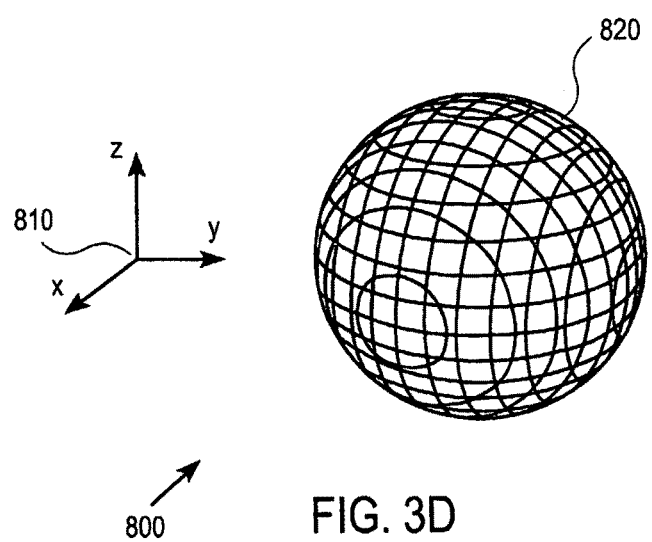
FIG. 3D shows a model of the hypothetical sphere of FIGS. 3A, 3B, and 3C with coordinate axes labeled.

FIG. 3D shows the 1D spherical object modeling system 800, with the coordinate reference frame 810 and the spherical object 820.

As one moves to slices of the sample away from the coil surface, the gradient is smaller, resulting in a narrower image. The phase gained by an element at position (x, z) by the first and second gradients separately is dependent on both the x and z position, however the total phase (subtracting the effect of the first) is determined by only the x position as shown by:

$$\phi_1 = Gxzt$$

$$\phi_2 = Gx(z+\Delta z)$$

$$\phi_{total} = Gx(\Delta z)$$

FIG. 2A is a plot of the calculated gradient strength at different distances from the coils, plotted as a function of position along the coils shown in the FIG. 2B coil geometry.
Method 2: Shim Pulses for Ex-Situ Imaging and Spectroscopy The method described in the previous section relies on precise hardware design and construction in order to achieve high-resolution images with or without chemical shift resolution. However, the strength of the gradient for a set amount of power is decreased considerably in this setup, decreasing the image resolution for a given power input (the strength of the effective gradient is scaled by Δz, the vertical distance between the two gradient coil sets). Another way to create a correct spatial field distribution is via the ex-situ shim pulses. This scheme works, as follows. Static field gradients from imaging gradient coils impose a spatial dependence on the spin precession frequency. Frequency selective pulses applied in the presence of static field gradients, therefore affect spins in a spatially selective way. Suppose one such RF pulse provides a phase shift to the spins, in a spatially dependent manner. If the gradients change before a second selective pulse is applied, another phase is given that depends on space. One can optimize the way the gradients are modulated so that this spatial dependence cancels inherent static field inhomogeneities, either resulting in an effectively homogeneous field, or providing a linear spatial dependence for imaging in one or more dimensions. 3D imaging can be accomplished by simultaneously applying $\vec{B}_0$ gradients in three directions. The $\vec{B}_1$ field can be inhomogeneous (as in the case of ex-situ) or homogeneous (for in situ cases).

In the case of ex-situ shim pulses for spectroscopy, the combination of ex-situ matching and shim-pulses relaxes the hardware requirements on both techniques: matching doesn't have to be "perfect" and the strength of the shim pulse gradients doesn't have to be as high. The way that the ex-situ shim pulse scheme works as follows: first the static magnetic field is mapped via NMR: a $\vec{B}_0$–$\vec{B}_1$ correlation NMR experiment in FIG. 4. Second, a coil geometry that to a first degree, matches the static field in the ex-situ case is built (in the in-situ case the coil is designed according to the experiment requirements it could be inhomogeneous is a single sided coil is desired, or a homogeneous coil can be used). For a given set of gradient coils, RF geometry and static field profile, the shim pulses are optimized to either produce a homogeneous or linearly varying field.

Figure 4:
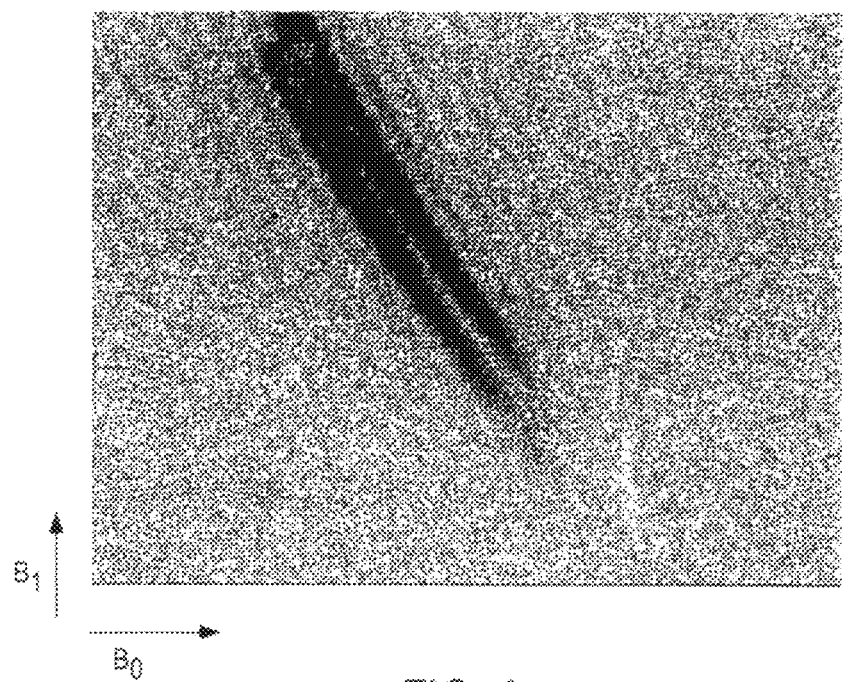
FIG. 4 shows an example of a $\vec{B}_0$ versus $\vec{B}_1$ correlation experiment. In the art, this is commonly expressed in a more simplified manner as a "$B_0B_1$" experiment.

FIG. 4 shows an example of a $B_0B_1$ experiment. The procedure for this is described in reference 9, V Demas, D Sakellariou, C Meriles, S Han, J Reimer, and A Pines, Proc. of the Natl. Acad. Sci. 101 (24), 8845-8847 (2004), which is hereby incorporated by reference in its entirety. A conical solenoid coil is used, and the sample is placed in a section where the RF field has a linear gradient. The static field also has a linear dependence, which is why the correlation is linear as well. In reference 9, the coil was designed purposely so that the field it produces reproduces the static field dependence so that the correlation results can be sheared and projected to yield the sample's spectrum. Here the idea is that we just use the known $\vec{B}_1$ field to locate the signal so that we accurately determine the static field value at an exact position unambiguously.

FIG. 4 shows a correlation between the static and RF fields. In the case of the matching experiments this correlation can be used to obtain spectral information, after careful construction of an RF coil to have an RF field variation that matches the static field variation. This correlation map can also be used to get an accurate field map of a static field, if one uses an RF coil with a well know and desired field profile (linear profile is the easiest choice, but it is not necessary). The correlation can be obtained either as described in the reference, by using the adiabatic double passage and adjusting of the scaling value between the two pulses, or via a nutation experiment, or via z-rotation pulses.

Figure 5:
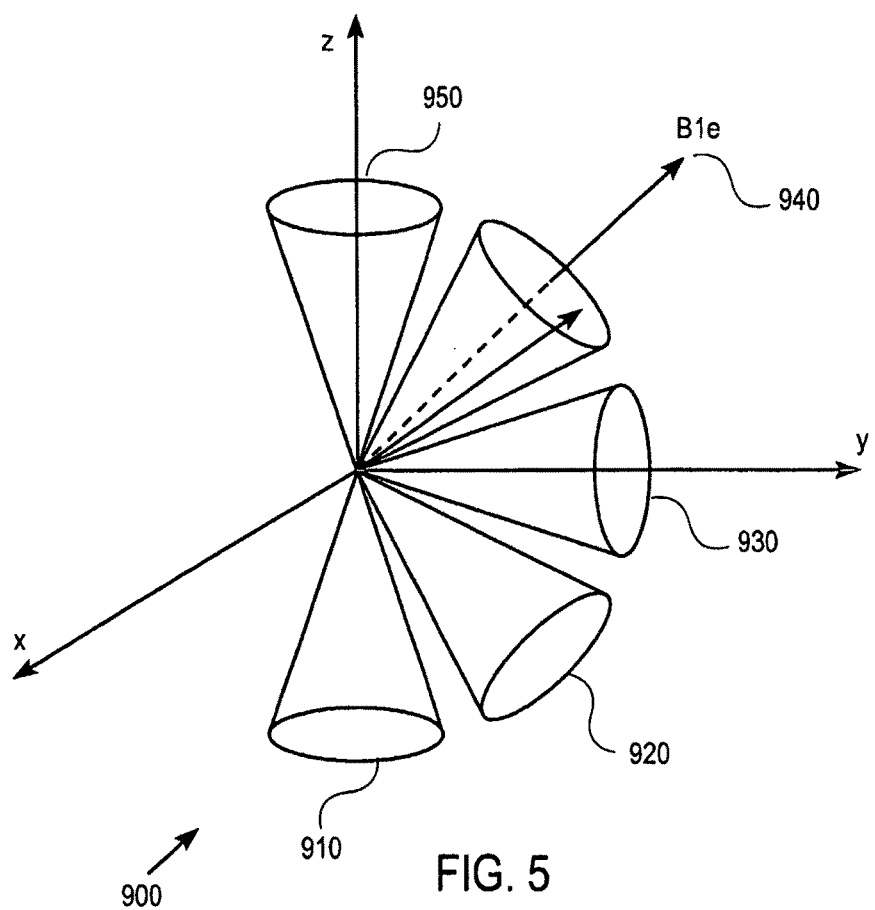
FIG. 5 depicts, after an adiabatic inversion, the phase of portions of the sample, depending upon the local effective field, given by the applied $\vec{B}_1$ as well as $\vec{B}_0$, which can be modulated with gradient pulses.

FIG. 5 shows that, after an adiabatic inversion, the phase of portions of the sample depend on the local effective field, given by the applied $\vec{B}_1$ as well as $\vec{B}_0$, which can be modulated with gradient pulses 900. Here shown are five "snapshots" of the effective field and attendant precessing nuclear magnetization. The adiabatic pulses slowly rotate the effective field, and thus the magnetization, away from thermal equilibrium. Initially, the rotating frame begins at −z (910), which progresses upward 920 to the +y axis 930, upward still to the positive z axis 950. The effective field B1e 940 is determined by the applied RF and the frequency offset in the rotating frame.

The phase of spin ensembles in the presence of an effective field, $\vec{B}_{EFF}$, is $$\phi(\vec{r}, t) = \gamma \int_0^\tau \sqrt{|\vec{B}_{EFF}(\vec{r}, t')|^2} \, dt'$$

$$= \gamma \int_0^\tau \sqrt{|\vec{B}_1(\vec{r}, t')|^2 + \left(\frac{\Delta\omega(\vec{r}, t')}{\gamma}\right)^2} \, dt'$$

The static field is measured during field mapping. As an example, the static field is assumed to have a quadratic dependence in two dimensions (x and z):

$$Y(x,z) = +Ax^2 + Bz^2$$

It should be noted that for other geometries of static field strength, other approximations would be used. This would be readily apparent to one skilled in the art.

A general form may be given to the time modulated gradient may be assumed (as a sum of sinusoidal waves)

$$G_{shim}(t) = \sum_{i=1}^n a_i \sin(\omega_i t + \phi_i)$$

with variables $a_i$, $\omega_i$, and $\phi_i$. A uniform normalized unit direction of the gradient may be described as $\vec{G}_{shim}$. This may be elaborated to include spatial inhomogeneities of the gradient as well. In this example, the basis functions for the approximation of $\vec{G}_{shim}$ are the sine functions, resulting in a Fourier sine series, with coefficients of each basis approximation $a_i$, $\omega_i$, and $\phi_i$. More generally, $G_{shim}(t)$ may be any function of time $f(t)$.

The RF pulses may be as a first approach adiabatic, where the amplitude and the frequency are modulated. A hyperbolic secant tangent pair for the amplitude and frequency modulated RF pulses is chosen for this example. The $\vec{B}_1$ field, or RF field, can have a spatial dependence, but it is not necessarily required for the methods described here to work.

$$\vec{B}_1(\vec{r},t) = \vec{B}_1^{max}(\vec{r}) \text{sech}(\beta t)$$

$\vec{B}_1(\vec{r},t)$ describes the shape of a particular pulse, which may be adiabatic, or nonadiabatic. In fact, $\vec{B}_1(\vec{r},t)$ may be modulated as a function of phase, amplitude, or both. $\vec{B}_1(\vec{r})$ reflects the geometry of the RF pulse, where sech(βt) reflects the time modulated portion of the RF signal, and here, the "sech" function is the hyperbolic secant. Here, β represents the frequency modulation of the $\vec{B}_1(\vec{r},t)$ field.

For hyperbolic secant pulses, a complex form representation is found in reference 12 as $\vec{B}_1(t) = B_1^0 (\text{sech}(\beta t))^{1+i\mu}$. The same usage for variables μ, β is used herein.

$$\omega_{RF}(t) - \omega_c = \mu\beta \tan h(\beta t)$$

$$\Delta\omega(\vec{r},t) = \omega_0(\vec{r}) - \omega_{RF}(t)$$

For shim pulses, one can set as the goal to create a phase that cancels that of the local inhomogeneity for a homogeneous overall effect. It is easy to project to imaging in the case the gradients are not pure, and the final goal is a phase that has a linear dependence in space.

We now minimize $\phi(\vec{r},t)$ below by varying the $a_i$, $\omega_i$, and $\phi_i$ of $G_{shim}(t)$ so that the local dephasing is effectively cancelled:

$$\phi(\vec{r}, t) =$$
$$\gamma \int_0^\tau \sqrt{|\vec{B}_1(\vec{r}, t')|^2 + \left(\vec{r} \cdot \vec{G}_{shim} G_{shim}(t') + \|\vec{B}_0(\vec{r})\| \frac{\Delta\omega(\vec{r}, t')}{\gamma}\right)^2} \, dt' -$$

$$(Ax^2 + Bz^2)\gamma t$$

Again, here we have used the saddle geometry field strength of $Ax^2 + Bz^2$. For other field geometries, other field strength approximation functions would be used.

It is readily apparent that such minimization may be accomplished with other $G_{shim}(t)$ functional bases, where coefficients of the bases may be minimized to effectively cancel the local dephasing.

Figure 6:
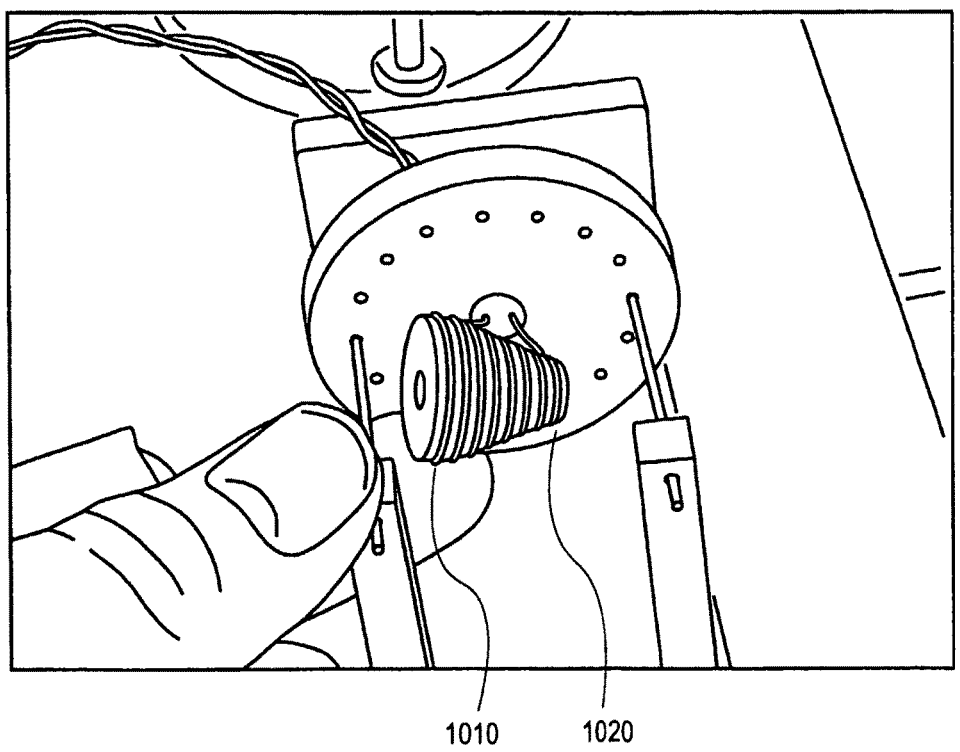
FIG. 6 illustrates an RF coil geometry producing a field with a well-known spatial dependence which can be used to "label" the position of the sample in space (and therefore the correlation experiment unambiguously gives the local $\vec{B}_0$ field value).

FIG. 6 shows a small (notice the human thumb) field calibrator coil system 1000 starting with wide diameter coil 1010, covering a cone shaped section down to a small diameter coils 1020. The simple jig fixture enables the coil to be rotated to arbitrary fixed angles.

Figure 7A:
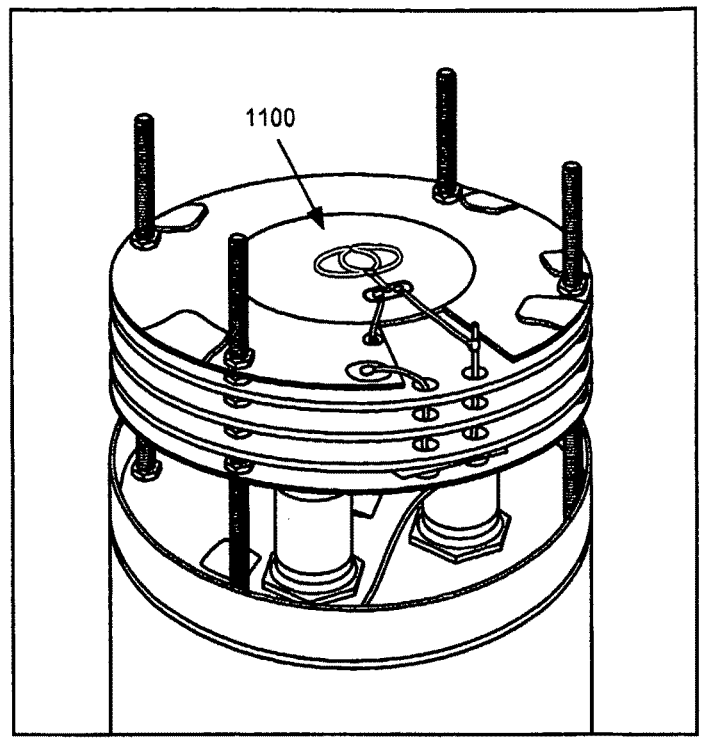
FIG. 7A is a sketch of an assembled three-dimensional scanning device as described herein for ex-situ NMR and MRI with inhomogeneous fields, containing a small RF probe.
Figure 7B:
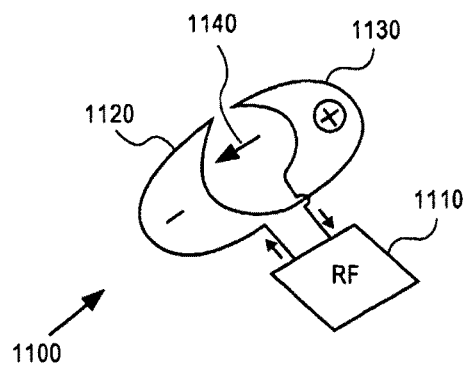
FIG. 7B is a schematic of a small RF probe.

FIG. 7A shows an implementation of a gradient coil, the ladder network, and an RF modulator. FIG. 7B shows the details of the modulator 1100, which comprises an RF source 1110 inputting power into an upward field on the left half 1120. The RF current is reversed on the right half 1130 of the devices, which results in a directed field 1140 being generated.

REFERENCES

The following reference are hereby incorporated by reference in their entireties:
1. D P Weitekamp, J R Garbow, J B Murdoch, A Pines, J. Am. Chem. Soc. 103, 3578 (1981).
2. J J Balbach et al., Chem. Phys. Lett. 277, 367 (1997).
3. Dan Demco, Current Opinion in Solid State and Materials Science 5, 195, (2001).
4. C A Meriles, D Sakellariou, H Heise, A Moule, A Pines, Science 293, 82 (2001).
5. Henrike Heise, Dimitris Sakellariou, Carlos A. Meriles, Adam Moule, and Alexander Pines, J. Mag. Reson. 156, 146-151 (2002).
6. Carlos A. Meriles, Dimitris Sakellariou, and Alexander Pines, J. Magn. Reson. 164, 177-181 (2003).

7. U.S. Pat. No. 6,674,282 B2 (2004)
8. Dimitris Sakellariou, Carlos Meriles, Alexander Pines, Comptes Rendus Academie des Sciences Physique 5, 337-347 (2004).
9. V Demas, D Sakellariou, C Meriles, S Han, J Reimer, and A Pines, Proc. of the Natl. Acad. Sci. 101 (24), 8845-8847 (2004).
10. D Topgaard, R W Martin, D Sakellariou, C A Meriles, A Pines, Proc. Natl. Acad. Sci. 101(51), 17576-17581 (2004).
11. J Perlo, V Demas, F Casanova, C Meriles, J Reimer, A Pines, and B Blumich, Science, 308 1279 (2005).
12. D. G. Norris, "Adiabatic Radiofrequency Pulse Forms in Biomedical Nuclear Magnetic Resonance", Max-Plank-Institute of Cognitive Neuroscience, Stephanstr. 1a, D-04103 Liepzig, Germany (2001).

This application has disclosed a technique capable of spectroscopy, imaging, and simultaneous spectroscopic imaging, in homogeneous to very inhomogeneous magnetic fields.

All publications, patents, and patent applications mentioned in this specification are herein incorporated by reference to the same extent as if each individual publication or patent application were each specifically and individually indicated to be incorporated by reference. Additionally, all patents and publications attached hereto and submitted herewith, even if not otherwise described in this application, are hereby incorporated by reference.

The description given here, and best modes of operation of the invention, are not intended to limit the scope of the invention. Many modifications, alternative constructions, and equivalents may be employed without departing from the scope and spirit of the invention.

We claim:

1. A method comprising:
   (a) exposing a sample volume to a static magnetic field ($\vec{B}_0$);
   (b) modulating a RF field ($\vec{B}_1$) that the sample volume is exposed to;
   (c) modulating a gradient field ($\vec{G}_{shim}(\vec{r},t)$) that the sample volume is exposed to, the gradient field being a function of a position vector ($\vec{r}$) associated with the sample volume and time (t), the static magnetic field, the RF field, and the gradient field forming an effective field ($\vec{B}_{EFF}(\vec{r},t)$);
   (d) detecting a nuclear magnetic resonance signal from the sample volume; and
   (e) minimizing a dephasing of the sample volume exposed to the effective field, the dephasing being caused by inhomogeneity in the static magnetic field.

2. The method of claim 1, wherein a degree of inhomogeneity in the static magnetic field is selected from the group consisting of greater than 10 parts per billion, greater than 100 parts per billion, greater than 1 part per million, greater than 10 parts per million, greater than 100 parts per million, greater than 0.001, and greater than 0.01.

3. The method of claim 1, wherein the static magnetic field is generated external to a volume enclosed by a source of the static magnetic field.

4. The method of claim 1, wherein the static magnetic field is generated internal to a volume enclosed by a source of the static magnetic field.

5. The method of claim 1, wherein the static magnetic field is generated by a magnet selected from the group consisting of an electromagnet, a superconductive electromagnet, and a permanent magnet.

6. A method comprising:
   (a) exposing a sample to a static magnetic field ($\vec{B}_0$);
   (b) modulating a RF field ($\vec{B}_1$) that the sample is exposed to;
   (c) selecting a particular spatial location ($\vec{r}_p$) of the sample;
   (d) modulating a gradient field ($\vec{G}_{shim}(t)$) that the particular spatial location of the sample is exposed to, the static magnetic field, the RF field, and the gradient field forming an effective field ($\vec{B}_{EFF}(\vec{r}_p,t)$);
   (e) detecting a nuclear magnetic resonance signal from excitation of a sample volume of the particular spatial location of the sample that is exposed to the effective field; and
   (f) minimizing a dephasing of the sample volume that is exposed to the effective field, the dephasing being caused by inhomogeneity in the static magnetic field.

7. The method of claim 6, further comprising:
   varying the particular spatial location.

8. The method of claim 6, wherein a degree of inhomogeneity of the static magnetic field is selected from the group consisting of greater than 10 parts per billion, greater than 100 parts per billion, greater than 1 part per million, greater than 10 parts per million, greater than 100 parts per million, greater than 0.001, and greater than 0.01.

9. The method of claim 6, wherein the static magnetic field is generated external to a volume enclosed by a source of the static magnetic field.

10. The method of claim 6, wherein the static magnetic field is generated internal to a volume enclosed by a source of the static magnetic field.

11. The method of claim 6, wherein the static magnetic field is generated by a magnet selected from the group consisting of an electromagnet, a superconductive electromagnet, and a permanent magnet.

12. The method of claim 6, wherein the magnet includes a pillow configuration magnet configured to at least partially surround one or more animal anatomical features selected from the group consisting of a head, a leg, an arm, an abdomen, a hand, and a body.

13. An apparatus comprising:
   a magnet configured to generate a static magnetic field;
   a first coil configured to generate an RF field;
   a second coil configured to generate a gradient field; and
   a processor, the processor configured to execute program instructions to:
   (a) generate with the magnet the static magnetic field that a sample is exposed to;
   (b) modulate with the first coil the RF field that the sample is exposed to;
   (c) select a particular spatial location of the sample;
   (d) modulate with the second coil the gradient field that the particular spatial location of the sample is exposed to, the static magnetic field, the RF field, and the gradient field forming an effective field;
   (e) detect a nuclear magnetic resonance signal from excitation of a sample volume of the particular spatial location of the sample that is exposed to the effective field; and
   (f) minimize a dephasing of the sample volume that is exposed to the effective field, the dephasing being caused by inhomogeneity in the static magnetic field.

* * * * *